United States Patent [19]

Haynes et al.

[11] Patent Number: 5,139,803
[45] Date of Patent: Aug. 18, 1992

[54] METHOD AND LIPOSOME COMPOSITION FOR THE STABILIZATION OF OXIDIZABLE SUBSTANCES

[75] Inventors: Lynn C. Haynes; Harry Levine, both of Morris Plains; John W. Finley, Whippany, all of N.J.

[73] Assignee: Nabisco, Inc., Parsippany, N.J.

[21] Appl. No.: 653,940

[22] Filed: Feb. 12, 1991

Related U.S. Application Data

[62] Division of Ser. No. 308,035, Feb. 9, 1989, Pat. No. 5,015,483.

[51] Int. Cl.⁵ .............................................. A23D 7/00
[52] U.S. Cl. ................................ 426/330.6; 426/602
[58] Field of Search ................. 426/73, 311, 603, 602, 426/330.6

[56] References Cited

U.S. PATENT DOCUMENTS

| | | | |
|---|---|---|---|
| 3,833,743 | 9/1974 | Morse | 426/311 |
| 3,887,698 | 6/1975 | McConnell et al. | |
| 4,016,100 | 4/1977 | Suzuki et al. | |
| 4,089,801 | 5/1978 | Schneider | |
| 4,133,874 | 1/1979 | Miller et al. | |
| 4,145,410 | 3/1979 | Sears | |
| 4,186,183 | 1/1980 | Steck et al. | |
| 4,193,983 | 3/1980 | Ullman et al. | |
| 4,217,344 | 8/1980 | Vanlerberghe et al. | |
| 4,221,732 | 9/1980 | Oette et al. | |
| 4,222,891 | 9/1980 | Okimoto et al. | |
| 4,235,792 | 11/1980 | Hsia et al. | |
| 4,235,871 | 11/1980 | Papahadjopoulos et al. | |

(List continued on next page.)

FOREIGN PATENT DOCUMENTS

| | | |
|---|---|---|
| 0216894 | 12/1984 | Japan . |
| 2107344A | 4/1983 | United Kingdom . |
| 8601404 | 8/1985 | World Int. Prop. O. . |

OTHER PUBLICATIONS

Swern 1979 Baileys Industrial Oil and Fat Products vol. I Fourth Ed. pp. 72-77.

"Polymerized Phosphatidylcholine Vesicles. Synthesis and Characterization," American Chemical Society, 12/7863/82/1504 (1982).

"Accelerated ripening of cheese using liposome-encapsulated enzyme," *International Journal of Food Science and Technology,* (1987) 22, 355-375.

"Procedure for preparation of liposomes with large internal aqueous space and high capture by reverse-phase evaporation", *Proceedings of the National Acad. of Science USA,* vol. 75, pp. 4194-4198 (1978).

"Encapsulation and stimulated release of enzymes using lecithin vesicles," *Intl. Journal of Food Science and Technology* (1987) 22, 707-723.

"Controlled Release of Food Additives," American Chemical Society, 0097-6156/88/0370-0177 (1988).

*Primary Examiner*—Carolyn Paden

[57] ABSTRACT

A stable, food-compatible liposome is prepared by dissolving a lipophilic material in a phospholipid followed by the addition of water or an aqueous solution and mixing by sonicating to produce a liposome having the lipophilic material encapsulated in the lipid bilayer. The preferred lipophilic materials include any readily oxidizable lipid and in particular the omega-3 fatty acid containing fish oils. Other lipophilic materials which can be encapsulated in the lipidic bilayer include flavorants, acidulants, preservatives and antioxidants. The resulting liposomes provide a stabilizing vehicle for the lipophilic materials to reduce the occurrence of oxidation and rancidity. Liposomes prepared according to the disclosed method exhibit none of the unpleasant odor and flavor characteristics normally associated with oxidized or rancid oils. The liposomes provide an extended shelf life of the unstable oils and can be added directly to the food product as a dispersion during the manufacturing stage or dried to a free flowing powder for later use.

40 Claims, 1 Drawing Sheet

U.S. PATENT DOCUMENTS

| | | |
|---|---|---|
| 4,261,975 | 4/1981 | Fullerton et al. . |
| 4,342,826 | 8/1982 | Cole . |
| 4,377,567 | 3/1983 | Geho . |
| 4,404,228 | 9/1983 | Cloosterman et al. . |
| 4,427,649 | 1/1984 | Dingle et al. . |
| 4,429,008 | 1/1984 | Martin et al. . |
| 4,448,765 | 5/1984 | Ash et al. . |
| 4,452,747 | 6/1984 | Gersonde et al. . |
| 4,483,921 | 11/1984 | Cole . |
| 4,483,929 | 11/1984 | Szoka . |
| 4,485,045 | 11/1984 | Regen . |
| 4,508,703 | 4/1985 | Redziniak et al. . |
| 4,522,803 | 6/1985 | Lenk et al. . |
| 4,528,226 | 7/1985 | Sweeny . |
| 4,532,089 | 7/1985 | MacDonald . |
| 4,564,475 | 1/1986 | Masaichiro . |
| 4,564,599 | 1/1986 | Janoff et al. . |
| 4,588,578 | 5/1986 | Fountain et al. . |
| 4,594,241 | 6/1986 | Rao . |
| 4,598,051 | 7/1986 | Papahadjopoulos et al. . |
| 4,619,794 | 10/1986 | Hauser . |
| 4,619,795 | 10/1986 | Cohen ................. 424/1.1 |
| 4,622,219 | 11/1986 | Haynes . |
| 4,622,294 | 11/1986 | Kung et al. . |
| 4,673,567 | 6/1987 | Jizomoto . |
| 4,695,554 | 9/1987 | O'Connell et al. . |
| 4,703,017 | 10/1987 | Campbell et al. . |
| 4,704,355 | 11/1987 | Bernstein . |
| 4,755,388 | 7/1988 | Heath et al. . |
| 4,764,392 | 8/1988 | Yasufuku et al. . |
| 4,804,539 | 2/1989 | Guo et al. . |
| 4,874,629 | 10/1989 | Chang et al. . |

METHOD AND LIPOSOME COMPOSITION FOR THE STABILIZATION OF OXIDIZABLE SUBSTANCES

This is a division of application Ser. No. 07/308,035, filed Feb. 9, 1989, which is now U.S. Pat. No. 5,015,483.

BACKGROUND OF THE INVENTION

1. Field of the Invention

The present invention relates to the production of liposomes containing lipophilic materials dissolved in the lipid layer of the liposome. More specifically, the invention is directed to the stabilization of oxidizable unsaturated lipophilic compounds by the encapsulation of the material in the lipidic layer of a liposome to retard or inhibit oxidation. The invention further relates to a lipophilic material stabilized by encapsulating the material in a liposome having a predetermined thermal transition temperature and shear resistance to withstand the physical treatments normally encountered in commercial food preparation. The liposomes can be used to introduce a readily oxidizable lipidic component to foods in a pure form. The liposomes offer a means whereby the lipophilic component can be easily dispersed in an aqueous phase. The liposomes can also be introduced to food compositions to slowly release the material dissolved in the lipidic layer over an extended period of time.

2. Brief Description of the Prior Art

Liposomes have been primarily used in recent years as delivery and carrier systems by encapsulating various compounds in the aqueous layer of the liposome. The emphasis of liposome development has been in the delivery of bioactive compounds. In the field of pharmaceutical and drug delivery, liposomes encapsulating drugs in the aqueous layer have been used successfully by suspending the liposome in a nonreactive carrier which can be injected directly into the treatment site to deliver an effective amount of the encapsulated drug.

Liposomes are essentially closed bilayer membranes in the form of vesicles or sacs containing an entrapped aqueous phase. Liposomes having a single bilayer membrane are referred to as unilamellar vesicles, whereas lipsomes having a number of concentric lipid bilayers separated by an aqueous phase are referred to as multilamellar vesicles. Recently, the attention on liposome preparation has focused on the liposomes with several bilayers, since these multilamellar vesicles demonstrate possibilities of encapsulating larger amounts of components than in the unilamellar vesicles.

Liposome preparation methods have been known for sometime. One of the earlier methods of preparing liposomes is described by Bangham et al. in *J. Mol. Bio.* Vol.13 pp. 238-252 (1965). According to that method, a phospholipid, such as phosphatidylcholine, is suspended in an organic solvent which is then evaporated to dryness, resulting in a waxy phospholipid deposit on the wall of the vessel. An aqueous phase containing a desired encapsulant is added to the reaction vessel, and mechanical means, such as ultrasonics, are used to disperse the resulting liposomes. The liposomes produced by this method are predominantly unilamellar vesicles (ULV). The liposomes have a lipidic bilayer, where the non-polar hydrophobic ends of the phospholipid orient themselves toward the center of the liposome bilayer, and the polar hydrophilic ends orient themselves towards the aqueous layer. Liposomes prepared according to this method are generally quite small, which restricts the ability to encapsulate large macromolecules.

As a consequence of these limitations, efforts have been made to increase the volume of the entrapped material. These methods have included the formation of inverse micelles or liposome precursors. The precursors are generally vesicles containing an aqueous phase surrounded by a monolayer of lipid molecules oriented so that the polar head groups are directed towards the aqueous phase. Liposome precursors are formed by adding the aqueous solution to be entrapped to a solution of an amphiphilic lipid in an organic solvent and sonicating the mixture. The organic phase is evaporated in the presence of the liposome precursors which associate with the excess lipid. The resulting liposomes are then dispersed in an aqueous phase. An example of such a process is disclosed in U.S. Pat. No. 4,224,179.

U.S. Pat. No. 4,235,871 to Papahadjopoulos discloses a reverse-phase evaporation process for making oligolamellar lipid vesicles, often referred to as reverse-phase evaporation vesicles or REVs. To prepare the REVs, a phospholipid is dissolved in an organic solvent contained in a flask, and the solvent is evaporated. The flask is purged with nitrogen, and the lipid is redissolved in the organic phase. The aqueous solution containing the material to be entrapped is added to the lipid solution. A homogeneous water-in-oil emulsion is then formed, and the organic solvent is evaporated until a gel remains. The gel is dispersed in an aqueous medium to convert the gel to a suspension. The preparation is finally dialyzed or centrifuged to remove non-encapsulated material and residual organic solvent.

In general, the larger a liposome, and the fewer layers it has, the more liquid it can encapsulate. Since the carrier liquid in which a liposome is dispersed can differ compositionally from that contained within the liposome itself, liposomes are potentially useful as biodegradable, relatively nontoxic vehicles for administering a component without risk of prematurely degrading the component, as might occur, for example, upon exposure to air or contact in the gastrointestinal tract.

Liposomes prepared from naturally occurring phospholipids have a tendency to be unstable during storage, thereby limiting their utility. This inherent instability results in a breakdown of the bilayers and the entrapped materials of the liposome diffusing into the surrounding liquid medium. This dispersing of the released materials can result in the contamination of the remaining liposomes by permeation of the materials from the surrounding medium into the liposome itself. The permeability characteristics of a liposome membrane bilayer can be altered by the addition of different stabilizers. For example, cholesterol can be mixed with other liposome-forming amphiphilic lipids to enhance the orientation of the amphiphilic lipids into a more orderly crystalline array. The more orderly arrangement stabilizes the bilayer and reduces permeation of materials.

A major use of liposomes to date has been in the medical field, by employing liposomes which entrap an effective amount of a water-soluble pharmaceutical compound and suspending the liposome in a pharmaceutically acceptable carrier. The advantages of using liposomes for this purpose arise from the fact that, when liposomes are injected into animals, they are taken up rapidly by the cells and intra-cellular lysosomes. Liposomes can be made to be relatively impermeable, and since they are rapidly taken up by the cells and removed from the circulatory system, the pharmaceutical remains concentrated in the liposome and unexposed to the plasma until such time as the liposomes are broken. This technology and knowledge primarily developed for the medical field offer alternative uses of liposomes, outside the delivery of pharmaceuticals, which have not been fully explored or utilized.

Liposomes may be prepared from a wide variety of lipidic compounds, including alkylamines, gangliosides, cardiolipin, and phospholipids Some of the more widely used lipids include the phospholipids wherein the phosphatidyl portion contains ester groups, for example $C_{14}$ to $C_{20}$, saturated or unsaturated, fatty acids. Specifically, liposomes may be prepared from any one or combination of dicetylphosphate, distearoylphosphatidic acid, dipalmitoylphosphatidylcholine, dimyristoylphosphatidylinositol, mono and dialkyl esters of phosphatidylserine, and dioleoylphosphatidylglycerol. In addition, lysophosphatides, wherein the fatty acid ester of $C_1$ or $C_2$ has been removed, can be mixed with the above-noted lipids to form liposomes. Other synthetic phosphatidyl compounds used include those wherein a sulfonium, phosphonium, or quaternary ammonium polar head moiety has been modified by the addition of hydrocarbon groups, particularly alkyl groups.

In the preparation and processing of food products, it is desirable to include various components or additives such as enzymes, vitamins, preservatives, acidulants or edible oils. Some of these additives can be combined in foods only in limited amounts due to their unpleasant flavor characteristics. In addition, some desirable additives, such as some vegetable oils and fish oils, are readily oxidizable and develop an unpleasant odor and flavor after a relatively short period of time. Some additives simply degrade over time or after exposure to oxygen and light and become ineffective. As a result of these inherent adverse characteristics, efforts have been made to modify the additives in some manner to disguise the flavor or stabilize the components. These efforts have not employed the formation of food-compatible liposomes which contain readily oxidizable substances in the lipidic bilayer.

One example of the prior art liposomes is U.S. Pat. No. 4,508,703, which discloses that a partially or totally hydrophobic substance may be added into the lipidic bilayer of liposomes or hydrated lamellar phases. The hydrated lipidic lamellar phases are prepared from a pulverulent mixture for producing liposomes which are primarily intended to be used in the release and delivery of drugs, as well as in the cosmetic and food industries. A mixture of amphiphilic and hydrophobic lipid constituents is produced in an organic solvent and atomized to produce a dry pulverulent material. Suitable amphiphilic lipids include phospholipids, glycolipids or phosphoaminolipids, such as egg or soya lecithin, a phosphatidylserine, a cerebroside or a sphingomyelin. The hydrophobic or partially hydrophobic constituents include sterols or esters thereof, such as cholesterol, aliphatic fatty acids or esters, aliphatic fatty amines, fatty acid acylated amides, polypeptides, vitamins or extracts of animal or vegetable origin. These hydrophobic constituents are added to the amphiphilic lipid to improve the physical characteristics of the resulting liposome, such as wall strength, permeability and stability. The liposomes and hydrated lipidic lamellar phases are produced by dispersing the pulverulent mixture in a suitable aqueous medium. The aqueous medium may contain water-soluble substances, such as proteins for use in foods or sodium carboxylate pyrrolidone for use in cosmetics.

U.S. Pat. No. 4,222,891 discloses a method of producing microcapsules for use in pressure-sensitive and carbonless duplicating papers. The microcapsules are prepared from an aqueous solution of gelatin, an anionic colloid material and oil droplets dispersed in the solution, via coacervation. The oils employed are the conventional oils used in the carbonless paper industry, such as fish or lard oils, vegetable oils, mineral oils or the synthetic oils. There is no suggestion of using the encapsulated oils in food products or encapsulating to stabilize the oils and prevent premature oxidation.

U.S. Pat. No. 4,404,228 relates to a free-flowing, non-caking material prepared by spray drying or drum drying a lipid-containing suspension followed by a comminuting step. The lipidic constituents are contained in the interstitial spaces of water-insoluble porous protein particles. The lipids employed may include vegetable, animal or marine fats, such as coconut, palm, palm kernel, fish, soybean, sunflower or tallow oils. The resulting dry product is used primarily as a milk replacer. The lipids in this type of product are intended to be readily soluble in water. The lipidic constituents are not protected from oxidation and do not provide for a sustained release of the lipidic constituents over a period of time.

U.S. Pat. No. 4,528,226 discloses a stretchable sheet having a coating of rupturable microscopic capsules that release fragrances. Enclosed within the microcapsules are water-insoluble oils, such as olive oil, fish oils, vegetable oils, sperm oils or mineral oils.

"Accelerated ripening of cheese using liposome-encapsulated enzyme" Kirby et al. *International Journal of Food Science and Technology* Vol. 22, pp.355-75 (1987) discloses the use of liposomes, to encapsulate an enzyme in the aqueous phase, for accelerating the ripening of cheese. Encapsulating the enzyme within the liposomes stabilizes the enzyme, such that it remains active longer. This produces a 100-fold increase in rate over conventional methods of ripening cheese. The liposomes are prepared by the dehydration/rehydration vesicle procedure (DRV), using egg phosphatidylcholine and soya lecithin dissolved in chloroform:methanol. The solution is dried by rotary evaporation to form a thin film of the lipid around the inside of the flask. The lipid is dispersed by swirling with distilled water to produce an opalescent dispersion. Neutrase dissolved in distilled water is then added to the dispersion, and the dispersion is frozen by swirling in a liquid nitrogen bath. The frozen dispersion of liposomes is then freeze-dried. DRV's were formed by adding distilled water to give a complete suspension of the material.

"Encapsulation and stimulated release of enzymes using lecithin vesicles" Kirby et al. *International Journal of Food Science and Technology,* Vol. 22, pp. 707-723 (1987) discloses lecithin vesicles prepared by dehydration/rehydration to encapsulate enzymes such as lysozyme and pepsin. The stimulated release of the enzymes under varying conditions and release patterns were examined.

Fats and oils are known to undergo a flavor change during storage, particularly at elevated temperatures. The flavor change is also associated with the unpleasant odors which make the fats unsuitable for human consumption. This condition of fats and oils is generally referred to as rancidity. The fats and oils which are prone to rancidity generally contain significant quantities of fixed oils and other lipids which undergo oxidation leading to the formation of primary, secondary and tertiary oxidation products. These oxidation products are responsible for the unpleasant odors and flavors. Factors which affect the rate of oxidation include the amount of oxygen present, the degree of unsaturation, presence of antioxidants, presence of pro-oxidants such as copper and iron, presence of heme-containing molecules and lipoxidase, nature of packaging, U.V. light exposure, and temperature of storage.

Highly unsaturated fats and oils undergo autoxidation. Autoxidation consists generally of a free radical chain reaction having an induction period, rapid formation of hydroperoxides, and finally the formation of the highly odorous reaction products. In general terms, a free radical is formed by an initiator such as singlet oxygen, ozone or superoxide radicals formed from the interaction of ferrous contaminants with triplet oxygen. Other initiators include UV radiation and enzymes, such as xanthine oxidase, which produce superoxide radicals. Peroxides are then formed which, in turn, break down to form perhydroxyl radicals or hydrogen peroxide. Finally, the reaction proceeds to form nonreactive molecules. The reaction is further complicated, in that the fatty-acid peroxides can decompose into odorous volatile compounds, such as saturated and unsaturated aldehydes and ketones. These low molecular weight carbonyls are usually the cause of the unpleasant odor and flavor. These volatile oxidation products can sometimes be removed in the refining process during deodorization. The non-volatile products, such as fatty acid hydroperoxides, tend to result in a lower oxidative stability of the oils.

The degree of unsaturation and the types of unsaturated fatty acids present are also important considerations in the rate of oxidation. For example, for the 18 carbon atom fatty acids having degrees of unsaturation 18:0, 18:1, 18:2 and 18:3, the relative rates of oxidation are in the ratio of 1:100:1200:2500. Thus the fatty acid having three points of unsaturation is 2,500 times more reactive than the completely saturated fatty acid.

Fish oils, and in particular the omega-6 and omega-3 fatty acid fish oils, are examples of highly unsaturated oils which may contain as many as five points of unsaturation and are readily oxidized. The unstable nature of fish oils explains the reason for their poor odor and flavor characteristics after a relatively short period of storage time. Because the odor and flavor of fish oils are so strong, it is very difficult to remove the odorous components to produce a food product which does not taste and smell fishy. In addition, it is very difficult to produce a fish oil-containing product which has an extended shelf life. Fish oil contains a large amount of highly unsaturated fatty acids such as eicosatetraenoic acid, eicosapentaenoic acid and docosahexaenoic acid. These fatty acids have been shown to be beneficial in controlling the cholesterol level in blood and in preventing thrombotic disturbances.

Because omega-3 fish oils are believed to reduce the risk of heart disease in humans and to lower cholesterol levels in the blood by encouraging the body to excrete more cholesterol, efforts are being made to produce a fish oil product, without the prominent odor and taste of fish, which can be used as a substitute for the saturated fats contained in many foods. One such example is disclosed in U.S. Pat. No. 4,764,392 relating to a margarine composition having a high content of refined unsaturated fatty acids from fish oils. The refining step includes a three stage molecular distillation process under vacuum at elevated temperature. The margarine is prepared by combining the refined fish oil with the usual vegetable oils, water, whey solids and emulsifiers conventionally used in margarine manufacture. The prepared margarine preferably contains 5-15% by weight of the refined fish oil, but may contain up to 40%. Above 15% fish oil, the margarine develops a fish oil taste and smell. As with other refining processes, this process has the disadvantage of not removing all of the non-volatile components from the fish oil, leading to distinctive fish odor and taste. In addition, the fish oil is still prone to oxidation and will again develop the fish odor and taste, thereby limiting the shelf life of the product.

U.S. Pat. No. 4,564,475 discloses a stable composition comprising a fish oil and a phospholipid such as lecithin as a stabilizing agent.

Other methods to prevent oxidation of fish oils have included the use of antioxidants and the encapsulation of the oil in gelatin capsules. These methods have not been effective in stabilizing fish oils for extended periods of time, because gelatin capsules do not provide an oxygen-impermeable barrier. Gelatin capsules generally have a particle size of about 100$\mu$ and are too large to be readily dispersed in an aqueous suspension. Moreover, gelatin capsules of this size result in a grainy texture which is undesirable in a food product. These capsules are ruptured upon mastication, thereby releasing the fish oil into a food. The release of fish oil that is not stabilized imparts an undesirable fish odor and flavor to a food. The gelatin capsules are easily rupturable and thus cannot be mixed in a dispersion, which is subjected to heat or high shear during processing, without release of the oil to the system.

In view of the favorable attributes of fish oil in the human diet, there is a need for a food-compatible product which is able to incorporate fish oil, but which is free from the distinctive fish odor or taste. There further is a need for a food-compatible composition which can stabilize labile components, prevent or inhibit oxidation of readily oxidizable lipophilic materials, and can be stored for extended periods of time without becoming rancid or losing its desirable characteristics.

The present invention is therefore directed to a food-compatible liposome composition containing highly oxidizable lipophilic materials dissolved in the lipid layer of a liposome. The liposomes prepared according to the invention provide a means to prevent or inhibit oxidation of the encapsulated lipophilic material. The invention is further directed to a suitable lipid-containing food product containing large amounts of the novel liposome composition but free from adverse effects on its flavor and odor.

SUMMARY OF THE INVENTION

The disadvantages and limitations of the prior art are obviated by providing an effective and efficient means of stabilizing readily oxidizable lipophilic materials. The present invention is particularly directed to the stabilization of readily oxidizable, labile lipophilic components, such as fish oils, by encapsulation of the components in the lipidic bilayer of liposomes. The resulting liposomes provide an excellent carrier for the lipophilic materials by placing them in intimate contact with oxygen-stable saturated fatty esters of the phosphatide. The lipid layer of the liposome further provides an oxygen barrier to inhibit propagation of free-radical chain reactions.

More particularly, the invention is directed to a method of effectively stabilizing readily oxidizable lipids. The liposomes prepared according to the invention provide a stable structure to encapsulate reactive and oxidizable lipids and to isolate them from the surrounding environment. The liposomes further provide a convenient and effective means for producing a stabilized lipid composition and a vehicle which can be readily dispersed in an aqueous medium or in a lipid medium. By encapsulating the oxidizable lipidic component in the lipid bilayer, the component does not come into direct contact with the aqueous surroundings, which reduces the risk of unwanted reactions for extended periods of time.

In the preferred embodiment of the invention, the encapsulated lipophilic material employed is an unsaturated triglyceride omega-3 fatty acid-containing fish oil which is deodorized and refined. The omega-3 fatty acid fish oils are dispersed in the phospholipid bilayer of the liposome to obtain a concentration of about 30% by total weight of the lipids in the system. Other unsaturated lipophilic components can include eicosatetraenoic acid, eicosapentaenoic acid, docosahexaenoic acid, oleic acid, linoleic acid, linolenic acid, and arachidonic acid.

When the lipophilic components to be encapsulated are highly unsaturated lipidic materials, such as the fish oils, it is preferred that the lipidic bilayer be made up of saturated phospholipids. The preferred phospholipids include, for example, the cholines such as phosphatidylcholine, myristoylphosphatidylcholine, stearoylphosphatidylcholine, palmitoylphosphatidylcholine, oleoylphosphatidylcholine, and linoleoylphosphatidylcholine. The aqueous layer or the lipidic layer may include various antioxidants or UV absorbers to further stabilize the oxidizable lipophilic component dissolved or dispersed in the lipidic layer. Examples of antioxidants and UV absorbers include the reduced form of the lipid-soluble, pyridine-linked dehydrogenases, lipid-soluble vitamins such as Vitamin E, acidulants, flavorants and preservatives.

The liposomes prepared according to the invention may be added directly to food preparations containing a high fat content, such as margarines, compound coatings, and other water-in-oil emulsions. The liposomes are readily dispersible in an aqueous phase or in an emulsion where a continuous aqueous phase is present, such as mayonnaise and other oil-in-water emulsions. The liposomes, when added to such compositions, are stable over extended periods of time and are resistant to moderate temperature changes. The liposomes may further be applied as a coating composition to food products to provide, for example, a flavoring or coloring agent. The liposomes are particularly suitable for dispersion in an aqueous system in which the entrapped lipophilic component would otherwise result in an undesirable phase separation. In this manner, it is possible to disperse the water-insoluble lipophilic component into an aqueous solution or aqueous phase.

According to the preferred embodiment of the invention, the liposomes are REVs prepared according to conventional practices. The method employed follows that disclosed in U.S. Pat. No. 4,235,871 by Szoka Jr. and Papahadjopoulos. The phospholipid, such as phosphatidylcholine and/or cholesterol, and the lipophilic material to be encapsulated are dissolved in an organic solvent, which is then evaporated in a flask by rotary evaporation. The system is then purged with nitrogen and the lipid redissolved in an organic solvent. The aqueous phase is then added, and the system is kept under nitrogen while being sonicated for 2-5 minutes in a bath-type sonicator until a homogeneous opalescent dispersion appears. The dispersion is placed in a rotary evaporator to remove the excess organic phase until a thickened gel-like mass is obtained. The method according to the invention has produced satisfactory liposomes containing up to 10% by total weight (i.e. liposomes and the residual water surrounding the liposomes) of the encapsulated lipophilic component. This corresponds to about 30% by total weight of the lipids present.

BRIEF DESCRIPTION OF THE DRAWINGS

The specification is to be interpreted in conjunction with the drawing, for which the following is a brief description.

DETAILED DESCRIPTION OF THE INVENTION

Figure 1:
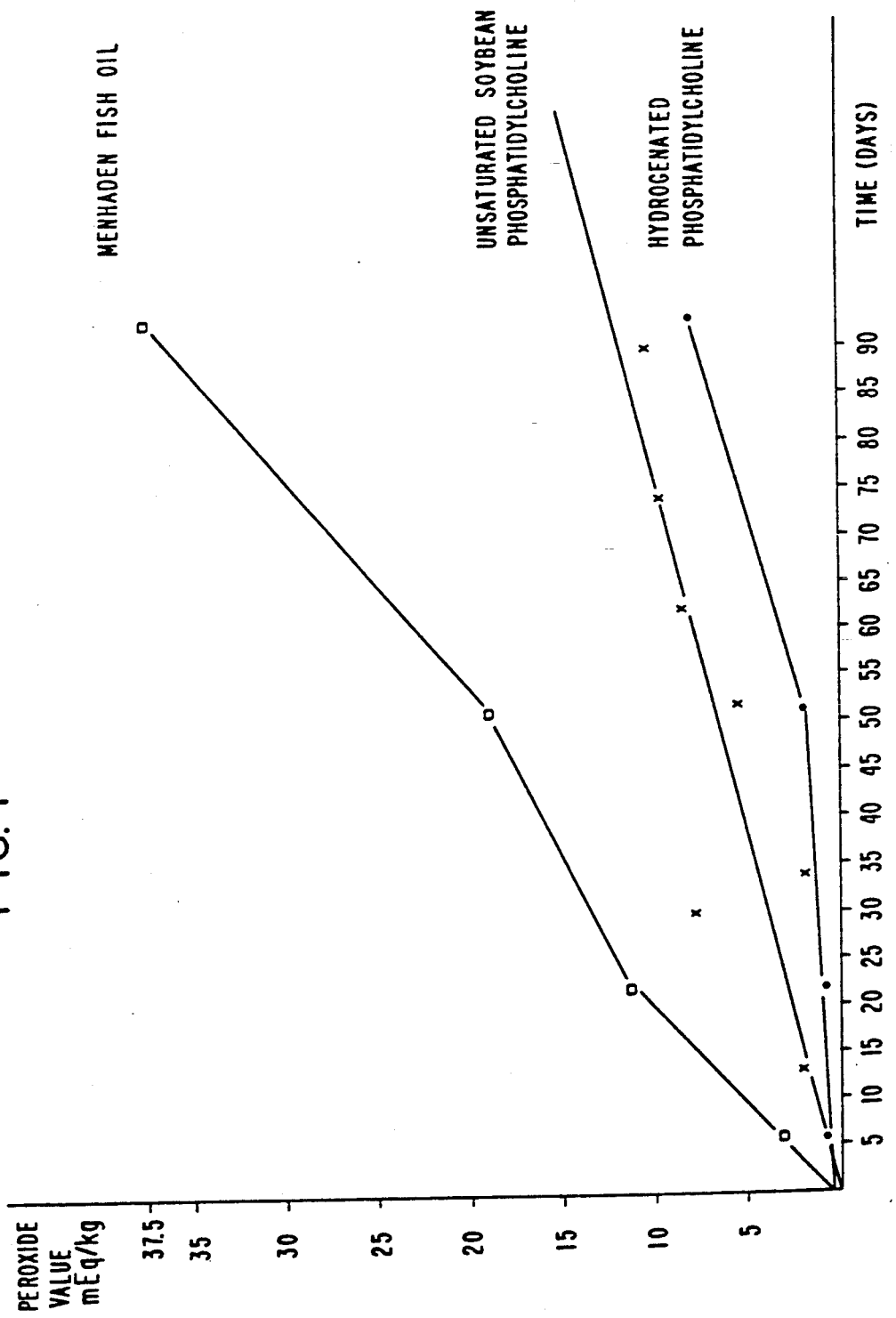
FIG. 1 is a graph comparing the peroxide values, expressed in milliequivalents per kilogram of lipid, over a period of 90 days for unencapsulated fish oil, fish oil encapsulated in liposomes made from soybean phosphatidylcholine, and fish oil encapsulated in liposomes made from hydrogenated phosphatidylcholine.

The present invention is directed to a novel method of forming a stabilizing medium for highly oxidizable materials, and in particular the oxidizable unsaturated lipophilic materials. The invention is further directed to a method of introducing the oxidizable materials into a food product. Of specific interest are the edible fats and oils, and particularly fish oils, used in the food industry, which are prone to becoming rancid and which exhibit a relatively short shelf life. Fish oils contain large amounts of highly unsaturated fatty acids and are therefore subject to very rapid oxidation and the development of the strong characteristic odor and flavor of fish oils.

The method according to the invention provides a usable composition which remedies these adverse characteristics of oxidizable lipophilic materials. In one embodiment of the invention, the liposomes may be in a dry powder form or as an aqueous dispersion, as discussed hereinafter in greater detail. As used throughout this disclosure, the term lipophilic component is intended to refer to a component which is soluble or miscible in the lipidic bilayer of a liposome and is the component of particular interest to be stabilized by being encapsulated in and carried by the liposomes. The solubility of the lipophilic component is dependent on several factors, including chain length, unsaturation, melting point and the like. The solubility of the lipophilic material will generally increase as the chemical and physical properties of the phospholipid and the lipophilic components become more alike. For example, the long-chain, highly unsaturated fish oils are generally more soluble in the phospholipids containing up to 60-70% linoleic acid and 6-13% oleic fatty acid esters. The triglycerides are generally more soluble in the phospholipids than the fatty acids and are therefore preferred.

Liposomes of the invention may be prepared by any of the conventional techniques, such as dehydration/rehydration and reverse phase evaporation (REV). The preferred method of the invention is by REV, since the vesicles generally contain a larger volume of entrapped materials. The lipophilic components, before encapsulation, are preferably purified and deodorized as necessary using standard known procedures.

The REVs according to the invention are prepared generally by the method disclosed in U.S. Pat. No. 4,235,871, which is hereby incorporated by reference, and Szoka et al., "Procedure for preparation of liposomes with large internal aqueous space and high capture by reverse-phase evaporation", *Proc. Natl. Acad. Sci. U.S.A.* Vol. 75, pp. 4194-4198 (1978).

The liposome-forming polar lipid containing the dissolved lipophilic component is dispersed in an organic solvent. The solvent is then evaporated under vacuum to produce a lipid film on the wall of the vessel. After redissolving the lipid in an organic solvent, an aqueous medium is then added to the vessel and mixed with the lipid to produce a liposome suspension. Mixing occurs by such means as homogenizing or sonicating at standard frequencies and time periods. The liposome dispersion according to the present invention can then be stored as a dispersion or dried by freeze drying to remove the excess water. The liposome powder can be stored and later rehydrated as desired and added directly to the other ingredients of the finished composition, as discussed hereafter in greater detail. The liposomes have the distinct advantages of being quite stable and providing an effective stabilizing means for reactive and oxidizable lipophilic materials. The liposomes can be easily dispersed in an aqueous medium, regardless of whether the liposomes are stored as an aqueous dispersion or as a dried powder.

In the preferred embodiment of the invention, the lipophilic material is a lipid oil containing a high degree of unsaturation. Since autoxidation of unsaturated fats and oils involves a chain reaction of the double bonds, it is desirable to have the lipidic bilayer of the liposome formed from a saturated phospholipid. It is believed that the saturated lipidic layer tends to "dilute" the unsaturation of the dissolved or encapsulated component. The dilution reduces the likelihood of formation of free radicals and reduces the number of available reaction sites for any radicals which do form. The oxidizable materials in the lipidic bilayer are isolated from the environment, thereby reducing the likelihood of exposure of the oxidizable material to oxygen. Since the encapsulated highly oxidizable lipophilic component is dispersed throughout the comparatively non-reactive lipidic bilayer of the discrete liposomes, propagation of the free-radical chain reaction from one unsaturated chain to another is inhibited, as is also the propagation of free radicals from one liposome to another.

A disadvantage of using saturated phospholipids when encapsulating unsaturated lipophilic materials is that the solubility of the lipophilic material to be encapsulated may be somewhat low. The low solubility thus limits the amount of the lipid that can be encapsulated. To overcome this lower loading capacity, small quantities of suitable additives such as glycerol are added to the lipid bilayer. Substantial increases in the amount of encapsulated lipid have been realized when glycerol is used in an amount corresponding to about 0.1 to 2 mole % of the phospholipid. Alternatively, the lipidic bilayer can be made up of a combination of suitable phospholipids or other liposome-forming lipidic components in which the unsaturated lipophilic materials are more readily soluble. The preferred lipidic materials employed in the bilayer are the phospholipids of choline such as egg phosphatidylcholine, dilauryloylphosphatidylcholine, dimyristoylphosphatidylcholine, dimyristoylphosphatidyl-choline, dipalmitoylphosphatidylcholine, distearoylphatidylcholine, 1-palmitoyl-2-myristoylphosphatidylcholine, 1-stearoyl-2-palmitoylphosphatidylcholine, 1-palmitoyl-2-stearoylphosphatidylcholine and dioleoylphosphatidylcholine.

In addition to the above phospholipids, a number of other lipids may be incorporated in the lipidic bilayer to reduce the permeability, strengthen the vesicle wall, and generally improve the physical characteristics of the liposome. Examples of such lipids may include sterols, cholesterol, aliphatic amines (such as long-chain aliphatic amines and carboxylic acids), long-chain sulfates and phosphates, dicetyl phosphate, butylated hydroxytoluene, tocopherol, retinol and isoprenoid compounds. The amounts will vary depending on the desired strength of the wall, the permeability of the encapsulated material through the wall, and the environment, but will generally not exceed a 1:1 ratio with the selected phospholipid.

When the liposomes are prepared for food use, it is desirable to reduce or eliminate the use of cholesterol as a stabilizer lipid. As an alternative, the saturated phosphatidylcholines having a chain length of 18 carbons and alpha-tocopherol have been found suitable for producing stable liposomes. The liposomes of the preferred embodiment of the invention have been found to be stable for the intended use, even in the absence of a stabilizer.

In addition, synthetic phospholipids containing either altered aliphatic portions, such as hydroxyl, branched carbon chains and cycloderivatives, ethers, amides, polyunsaturated derivatives, and halogenated derivatives, or altered hydrophobic portions containing carbohydrate, glycol, phosphate, phosphonate, quaternary amine, sulfate, sulfonate, carboxy, amine, sulfhydryl, and imidazole groups can be used to form liposomes in which the unsaturated lipophilic materials are more readily soluble. Several other phospholipids have been found useful in forming liposomes and can be employed depending on the material to be encapsulated and the environment in which they are to be used. By way of non-limiting examples, these phospholipids include phosphatidic acid, phosphatidylserine, phosphatidylethanolamine, spingolipids, phosphatidyl- glycerol, sphingomyelin, cardiolipin, glycolipids, gangliosides, cerebrosides, such as dilauryloyl phosphatidylglycerol, dipalmitoylphosphatidyl glycerol, distearoylphosphatidylglycerol, dioleoylphos- phatidylglycerol, dimyristoylphosphatidic acid, dipalmitoyl phosphatidic acid, dimyristoylphosphatidylethanolamine, dipalmitoylphosphatidylethanolamine, dimyristoylphosphatidylserine, dipalmitoylphosphatidylserine, dipalmitoylsphingomyelin, and distearoylsphingomyelin.

In an alternative preferred embodiment of the invention, the phospholipid has a transition temperature slightly above temperatures required for processing the food product, such that the liposome will maintain its integrity. Depending on the final application and the type of food product, the liposome can have a transition temperature slightly below body temperature. In this manner, the liposome may be solid at room temperature and fluid when consumed to increase the rate of release of the lipophilic component to provide proper taste and mouth feel. When fish oils are to be encapsulated, the phospholipid is selected such that the transition temperature is slightly above body temperature, whereby the liposomes will not dissolve or rupture in the mouth, but will rupture in the intestinal tract to release the fish oil.

The transition temperature can further be controlled by the addition of suitable additives as are known in the art. When the liposome encapsulates a flavoring agent, it is desirable to have the phase transition temperature slightly below body temperature. When the food product incorporating the liposome is eaten, the liposome will rupture to release the flavoring agent. The shelf life of the liposome can be extended when the transition temperature is selected to withstand the anticipated storage conditions and expected temperature changes. Liposomes are generally considered to be solid at temperatures below the characteristic gel-liquid crystalline phase transition temperature of the phospholipid and fluid when above the transition temperature.

Although the preferred embodiment is directed to the encapsulation of fish oils, and in particular the omega-3 fatty acid-containing fish oils, the liposomes according to the invention may incorporate any substance which is soluble or miscible in the lipid bilayer. The oxidizable lipids which are common in the food industry and which may, by way of example, be incorporated in the lipid layer include eicosatetraenoic acid, eicosapentaenoic acid, docosahexaenoic acid, oleic acid, linoleic acid, linolenic acid, and arachidonic acids. The lipophilic material in the lipidic bilayer of the liposome is generally in the range of 10 to 30% by weight of the total lipids in the system. Other materials which may be dissolved in the lipidic bilayer of the liposome and are of particular interest include lipid-soluble vitamins, glycerol, acidulants, preservatives, flavorants, antioxidants, UV absorbers and tropicalizing agents for confectionery coatings and compounds.

EXAMPLE I

A deodorized and refined menhaden fish oil having a high omega-3 acid content was selected to be dissolved in and carried by the lipid bilayer of a liposome formed from an unsaturated phospholipid. The liposome was prepared by dissolving 7.5 g of unsaturated soybean phosphatidylcholine (sold under the tradename Infusol) in 200 ml of reagent-grade chloroform containing 3.0 g of refined and deodorized menhaden fish oil in a 1 liter round-bottom flask at room temperature. To the flask, 66 ml of distilled water was added and mixed using a laboratory-scale homogenizer for about 2 minutes until a dispersion was formed. The dispersion was then placed in a rotary evaporator at about 40°-50° C. for about 40-60 minutes under vacuum to remove the solvent Residual chloroform was removed by purging with nitrogen while shaking to break up the aggregates. The liposomes appeared as a tan-colored viscous gel. The resulting gel consisted of about 10% fish oil, 25% phospholipid, and 65% water by volume. The liposomes contained about 30% of encapsulated menhaden fish oil by weight of total lipid, which corresponds to about 10% of the total weight of the liposomes including residual water surrounding the liposome. Electron microscopy confirmed the presence of unilamellar and multilamellar lipsomes. The liposome dispersion had substantially no fish odor or flavor.

EXAMPLE II

A liposome preparation was made using a hydrogenated phosphatidylcholine sold under the tradename Phospholipon H-100. Phospholipon has a phase transition temperature of about 552° C., which is higher than the Infusol. A solution of 7.5 g Phospholipon in 200 ml of chloroform was mixed with 3.0 g of refined menhaden fish oil. To the solution, 66 ml of distilled water and 0.68 g of glycerol were added while mixing using a laboratory-scale homogenizer. The dispersion was transferred to a rotary evaporator at about 60°-63° C. under vacuum to remove the chloroform. The resulting liposomes contained about 30% encapsulated menhaden fish oil by total weight of lipids present in the system. This corresponds to about 10% by weight of the liposome including residual water adhering to the outer surfaces of the liposome The lipid particles were found to have a diameter generally ranging between 0.2 and $2\mu$, with a few as large as $20\mu$, as determined by laser light scattering. The smaller particles are believed to be unilamellar liposomes, while the larger particles, greater than $1.0\mu$, are believed to be multilamellar liposomes.

EXAMPLE III

A comparative study of the oxidative stability of the unencapsulated fish oil and the liposome-encapsulated fish oil prepared according to Examples I and II was made by measuring the peroxide value in milliequivalents per kilogram of lipid. The change in peroxide value provides an indication of the extent of oxidation of the lipids during storage The control sample of menhaden fish oil and the liposome preparations were stored at about 4° C. and brought to room temperature before determining the peroxide value using standard laboratory techniques. FIG. 1 shows the changes in the peroxide value over a period of 93 days for each sample. As can be seen, the control sample containing the unencapsulated fish oil demonstrated a rapid and substantial increase in the peroxide value, reaching a value of 37.5 mEq/Kg after 93 days. The liposome-encapsulated fish oil demonstrated a substantially lower peroxide value of 11 mEq/kg for Infusol-encapsulated fish oil and 8 mEq/kg for Phospholipon-encapsulated fish oil after essentially the same length of time. The data demonstrate a stabilizing effect on the liposome-encapsulated fish oil. The unencapsulated fish oil is shown to oxidize 3 and 4 times as fast as the encapsulated fish oil. In addition, the liposomes formed from the saturated phospholipid were shown to have a greater stabilizing effect than the liposomes from the unsaturated phospholipid.

In addition to the phospholipid, a sterol compound, such as cholesterol, a saturated phosphatidylcholine or alpha-tocopherol (vitamin E), can be added to stabilize the lipid wall of the liposome. The cholesterol has the effect of orienting the amphiphilic lipids to a more orderly crystalline array within the bimolecular layers, making the lipid layer much more resistant to diffusion of the encapsulated component. A suitable stabilizing amount is usually about 0.5% to about 3.0 % by weight of the phospholipid, but may also be in a mole ratio of 1:0.25 to 1:1, depending on the intended environment. When cholesterol is used, the ratio is generally quite small, such that the final amount of cholesterol present in the food product does not exceed the cholesterol level normally present. The liposomes prepared by the above method have been found to be sufficiently stable and do not require a stabilizer.

The liposomes containing the entrapped lipophilic material in the lipidic bilayer can be used in the form of an aqueous dispersion by adding the liposomes directly to the other ingredients in the formation of a food product. For example, in the preparation of a margarine, the liposomes containing encapsulated fish oil are mixed with the emulsion and molded by conventional means.

The margarine emulsion will typically comprise 70 to 80% hydrogenated and interesterified vegetable oils, and an aqueous phase in the range of 20 to 30% containing water, proteinaceous materials such as skim milk powder, whey protein, casein, sodium caseinate, or soy protein, preservatives, emulsifiers, hydrophilic colloids, and flavorants. The liposomes in the preferred form of the invention are combined with the emulsion in amounts to produce a margarine having a final fish oil content of between 3 and 5% by weight of lipids in the system.

By way of a non-limiting example, a margarine composition is prepared by combining a hardened vegetable oil containing hydrogenated soybean oil and palm oil in a vessel and heating to slightly above the melting point A suitable amount of lecithin, flavorants and colors are added to the fat portion. The water phase is added to the melted fat. The water phase contains salt, whey powder, potassium sorbate, citric acid alginate, and liposomes containing encapsulated fish oil as prepared in Example I. A sufficient amount of liposomes containing encapsulated fish oil is added such that the final margarine product has 3 to 5% by weight fish oil. The margarine emulsion is soft and readily spreadable and does not exhibit oil or water separation. The liposomes are able to withstand the shear stresses during mixing and heat treatment in the process. Since the liposomes are readily dispersible in the aqueous phase, the amount of fish oil to be added to the margarine composition is not limited by the characteristics of the liposomes, and fish oil can be added in any desired amount.

The novel liposomes, when prepared according to the present invention, can also be used as a means to control the release of various encapsulated components over time For example, when the lipophilic material dissolved in the lipidic bilayer is a preservative, the liposome can be added to the food product as a dry powder or as a dispersion. By selecting the particular lipid of the lipid bilayer, the stability of the liposome wall can be controlled so that the wall breaks down at a reasonably predictable rate and at predetermined temperatures to release the preservative to the food product over an extended period of time.

Liposomes prepared from some phosphatidylcholines and other polar lipids may not be particularly stable to high shear. To improve the resistance of the liposomes to high shear, the phosphatidylcholine can contain an unsaturated fatty acid, which after liposome formation is covalently crosslinked by subjecting it to U.V. radiation. The exterior wall of the liposome is thus effectively polymerized to improve the shear stability of the liposomes.

Liposomes prepared from glycerophosphorycholine, bis-[12(methacryloyl) oxydodecanoyl] L-α-phosphatidylcholine, or 1-palmitoyl-2-[12(methacryloyloxy) docecanoyl]-L-α-phosphatidylcholine are particularly suitable for cross-linking Polymerization of the lipid bilayers, when formed from these phospholipids, is effectively carried out by direct U.V. irradiation at about 254 nm. Generally 1-3 hours is required to complete polymerization.

When the lipophilic material to be encapsulated is a highly unsaturated fatty acid, it is generally not desirable to subject the liposome to U.V. radiation, as this will tend to increase the rate of degradation of the unsaturated lipophilic component dissolved in the lipid bilayer In this type of liposome, the shear stability can be improved by the addition of chemically reactive cross-linking agents such as glutaraldehyde or by the addition of stabilizing agents such as cholesterol or other polar phospholipids as are known in the art.

To further enhance the resistance to oxidation of the encapsulated material, the lipid layer and/or the aqueous layer may further include an antioxidant or oxygen scavenger. Typical antioxidants include ascorbic acid, ascarbyl palmitate, butylated hydroxy anisole (BHA), butylated hydroxy toluene (BHT), EDTA, citric acid, propyl gallate, tocopherols, enzymes, and others as are well known in the art.

As a further embodiment, the lipidic bilayer of the liposome may include a desired amount of a lipid capable of releasing a hydrogen ion to further stabilize the oxidizable unsaturated lipophilic material. The preferred lipids are those which contain a vicinal amino or vicinal hydroxyl group along the polar head region of the lipid molecule. For example, in the instance of vicinal amino groups, a glycolipid having a galactosamine or glycocyamine residue is a suitable lipid. More commonly, the lipids will have a vicinal hydroxyl group at the polar head region. The preferred lipids include the glycolipids such as lactosyl lexosyl ceramide, galoctocerebroside, gangliosides, and trihexosylceramide, and phosphatidylinositol. When the lipid bilayer of the liposome is to include a lipid capable of releasing a hydrogen ion, it is preferred that the lipid be combined with the other lipids in a molar amount of about 10%. By including a suitable amount of the lipids in the lipidic bilayer, a source of donatable hydrogen ions is provided to the lipidic bilayer. It is generally understood that the ability to donate hydrogen ions provides a means of removing the active radicals from the autoxidation chain reaction.

While the invention has been described in connection with specific embodiments, it will be understood that it is capable of further modification. This application is intended to cover any variations, uses or adaptations of the invention following principles of the invention as set forth above. Any departure from the present disclosure, which is within the known or customary practice of those skilled in the art to which this invention pertains, shall be considered to be within the scope of the invention and limits as set forth in the following claims.

What is claimed is:

1. A margarine composition having a high content of at least one highly unsaturated lipid, said margarine composition including liposomes comprising at least one entrapped aqueous material and at least one polar lipid bilayer with a highly unsaturated lipid dissolved therein.

2. The margarine composition of claim 1 wherein said highly unsaturated lipid is a fatty acid selected from the group consisting of eicosatetraenoic acid, eicosapentaenoic acid, docosahexaenoic acid, arachidonic acid, oleic acid, linoleic acid, linolenic acid, and the triglycerides thereof.

3. The composition of claim 1 wherein said highly unsaturated lipid is a refined fish oil.

4. The margarine composition of claim 1 wherein the polar lipid is selected from the group consisting of lecithin, cephalin, dipalmitoylphosphatidylglycerol, distearoylphosphatidylcholine, sphingomyelin, phosphatidic acid, phosphatidylserine, phosphatidylinositol, phosphatidylcholine, phosphatidylethonolamine, cholesterol, dipalmitoylphosphatidylcholine, and mixtures thereof.

5. The margarine composition of claim 4 wherein the lipid bilayer further includes a stabilizing amount of a sterol.

6. The margarine composition of claim 1 wherein the unsaturated lipid is present in the liposome in an amount of about 0.1%-10% by total weight of the liposome.

7. The margarine composition of claim 1 wherein the liposome is present in an amount sufficient to obtain about 3-5% of the unsaturated lipid by weight of the margarine.

8. The margarine composition of claim 1 wherein the liposome further includes glycerol.

9. The margarine composition of claim 1 wherein said liposomes are a mixture of unilamellar and multilamellar liposomes.

10. A food-compatible, stabilized, oxidation-resistant composition comprising liposomes, said liposomes comprising at least one entrapped aqueous material and at least one lipid bilayer formed from a polar phospholipid having an unsaturated lipophilic material dispersed into the lipid bilayer, wherein said unsaturated lipophilic material comprises at least one member selected from the group consisting of a fish oil, vegetable oil or a fatty acid.

11. The composition of claim 10 wherein the unsaturated lipophilic material is present in an amount of about 0.1%-10% by total weight of the liposome.

12. The composition of claim 10 wherein the unsaturated lipophilic material is present in an amount of about 10-30% by weight of the polar lipid and lipophilic material.

13. The composition of claim 10 wherein said lipophilic material comprises a fatty acid selected from the group consisting of eicosotetraenoic acid, eicosopentaenoic acid, arachidonic acid, oleic acid, docosahexaenoic acid, linolenic acid, linoleic acid, and the triglycerides thereof.

14. The composition of claim 13 wherein the polar lipid is a saturated phospholipid.

15. The composition of claim 14 wherein said sterol is cholesterol or cholesterol acetate and is present in an amount of about 3 to 5% by weight of the polar lipid.

16. The composition of claim 13 wherein the polar lipid includes a stabilizing amount of a sterol.

17. The composition of claim 13 wherein the polar lipid includes a stabilizing amount of alpha-tocopherol of about 3 to 5% by weight of the polar lipid.

18. The composition of claim 10 wherein the polar lipid comprises at least one substance selected from the group consisting of phosphatidylcholine, phosphatidic acid, cholesterol, phosphatidylethanolamine, dipalmitoyl phosphatidylglycerol, distearoylphosphatidylcholine, hydrogenated phosphatidylcholine and phosphatidylinositol.

19. The composition of claim 10 wherein the liposomes are a mixture of unilamellar and multilamellar vesicles.

20. The composition of claim 10 wherein the liposomes have an average particle size between about 0.2 and 2μ.

21. The composition of claim 10 wherein the liposomes further contain glycerol in an amount of about 0.1 to 2.0 mole % by weight glycerol of the phospholipid.

22. The composition of claim 10 wherein the aqueous layer of the liposomes includes an oxygen scavenger selected from the group consisting of enzymes and ascorbic acid.

23. The composition of claim 10 wherein the polar lipid further includes a hydrogen-donating phospholipid selected from the group consisting of lactosylceramide, galoctocerebroside, gangliosides, trihexosylceramide and phosphatidylinositol.

24. The composition of claim 10 wherein said composition is a dry pulverulent composition.

25. The composition of claim 10 wherein said composition is an aqueous liposome dispersion.

26. A method of stabilizing and inhibiting the oxidation of an edible oxidizable lipophilic material comprising the steps of:
   a) combining an edible oxidizable lipophilic material with a polar phospholipid in an amount of about 10 to 30% by weight to produce a lipid mixture wherein the lipophilic material comprises at least one member selected from the group consisting of fish oil, vegetable oil or unsaturated fatty acid;
   b) combining the lipid mixture of step (a) with an aqueous component in an amount sufficient to form a dispersion; and
   c) mixing the lipid mixture and aqueous component to form a liposome dispersion wherein said oxidizable lipophilic material is dispersed in a phospholipid layer of liposomes in said liposome dispersion.

27. The method of claim 26 wherein said lipophilic component and phospholipid are dissolved in an organic solvent.

28. The method of claim 27 further comprising the step of removing the organic solvent under vacuum from the liposome dispersion.

29. The method of claim 26 wherein the edible lipophilic material is a fatty acid selected from the group consisting of eicosatetraenoic acid, eicosapentaenoic acid, docosahexaenoic acid, arachidonic acid, oleic acid, linoleic acid, linolenic acid, and triglycerides thereof.

30. The method of claim 26 wherein the phospholipid comprises at least one phospholipid selected from the group consisting of lecithin, cephalin, dipalmitoyl phosphatidylglycerol, distearoyl phosphatidylcholine, sphegomeyline, phosphatidic acid, phosphatidylserine, phosphatidylinositol, phosphatidylcholine, phosphatidylethanolamine, cholesterol, dipalmitotyl phosphatidylcholine, and mixtures thereof.

31. The method of claim 26 further comprising the step of sonicating the dispersion at a frequency of about 50 KHz for about 3-5 minutes to form said liposome dispersion.

32. The method of claim 26 wherein the phospholipid is a saturated phospholipid.

33. The method of claim 26 wherein the polar lipid further includes a stabilizing amount of cholesterol or cholesterol acetate and is present in an amount of about 3 to 5% by weight of the polar lipid.

34. The method of claim 26 wherein in the liposome includes a stabilizing amount of alpha-tocopherol of about 3 to 5% by weight of the polar lipid.

35. The method of claim 26 wherein the liposomes are a mixture of unilamellar and multilamellar vesicles.

36. The method of claim 26 the liposomes have an average particle size of about 0.2 to 2μ.

37. The method of claim 26 wherein the polar lipid further includes an oxygen scavenger.

38. The method of claim 26 wherein the polar lipid further includes a hydrogen-donating phospholipid selected from the group consisting of lactosylceramide, galoctocerebroside, gangliosides, trihexosylceramide and phosphatidylinositol.

39. A food-compatible, stabilized, oxidation-resistant composition comprising liposomes including an unsaturated edible fat or oil, said liposomes comprising at least one entrapped aqueous material and a lipid bilayer formed from a polar phospholipid having said unsaturated fat or oil and about 0.1% to 2.0% by weight glycerine dispersed therein.

40. A food product comprising liposomes, said liposomes comprising at least one entrapped aqueous material and at least one lipid bilayer formed from a polar phospholipid having an unsaturated lipophilic material dispersed in the lipid bilayer, wherein said unsaturated lipophilic material comprises at least one member selected from the group consisting of a fish oil, vegetable oil or a fatty acid.

* * * * *